United States Patent
Shimaoka

(10) Patent No.: US 9,261,448 B2
(45) Date of Patent: Feb. 16, 2016

(54) PARTICLE SIZE DISTRIBUTION MEASURING APPARATUS

(71) Applicant: SHIMADZU CORPORATION, Kyoto, Kyoto (JP)

(72) Inventor: Haruo Shimaoka, Nara (JP)

(73) Assignee: SHIMADZU CORPORATION, Kyoto (JP)

( * ) Notice: Subject to any disclaimer, the term of this patent is extended or adjusted under 35 U.S.C. 154(b) by 20 days.

(21) Appl. No.: 14/317,437

(22) Filed: Jun. 27, 2014

(65) Prior Publication Data

US 2015/0377761 A1    Dec. 31, 2015

(51) Int. Cl.
*G01N 21/00* (2006.01)
*G01N 15/02* (2006.01)

(52) U.S. Cl.
CPC .................. *G01N 15/0211* (2013.01)

(58) Field of Classification Search
CPC ............. G01N 15/0205; G01N 15/0211
USPC .................................... 356/335–343
See application file for complete search history.

(56) References Cited

U.S. PATENT DOCUMENTS

| | | | | |
|---|---|---|---|---|
| 6,417,920 B1* | 7/2002 | Shimaoka | .......... | G01N 15/0205 356/336 |
| 2003/0016356 A1* | 1/2003 | Adachi | ................ | G01N 1/2273 356/336 |
| 2010/0012496 A1* | 1/2010 | Tsunazawa | ............. | B03C 5/005 204/547 |
| 2010/0201982 A1* | 8/2010 | Moriya | .............. | G01N 15/0211 356/335 |
| 2012/0258547 A1* | 10/2012 | Von Drasek | ....... | G01N 21/6486 436/172 |

FOREIGN PATENT DOCUMENTS

| | | | |
|---|---|---|---|
| JP | 08178825 A | * | 7/1996 |
| JP | 09015135 A | * | 1/1997 |
| JP | 09-072841 A | | 3/1997 |

* cited by examiner

*Primary Examiner* — Sang Nguyen
(74) *Attorney, Agent, or Firm* — Sughrue Mion, PLLC

(57) ABSTRACT

A particle size distribution measuring apparatus having: a light intensity distribution obtaining unit for obtaining the light intensity distribution that occurs when the sample cell is irradiated with light for measurement from a light source through detection by a detector; and a particle size distribution calculating unit for calculating the particle size distribution of the particles to be measured included in the sample by using the light intensity distribution obtained by the light intensity distribution obtaining unit, the temperature adjusting member for adjusting the temperature of the sample cell is movable between a first location along the light path around the sample cell and a second location that is outside the light path, and the temperature adjusting member is moved to the second location when the sample is irradiated with the light for measurement from the light source.

4 Claims, 4 Drawing Sheets

PARTICLE SIZE DISTRIBUTION MEASURING APPARATUS

TECHNICAL FIELD

The present invention relates to a particle size distribution measuring apparatus using a sample cell, and in particular, to a laser diffraction-type particle size distribution measuring apparatus for measuring the particle size distribution of particles in a small amount of sample containing a high concentration of particles.

BACKGROUND ART

In a laser diffraction-type particle size distribution measuring apparatus, particles in a state of dispersion in a medium are irradiated with a laser beam (measuring light) so that the spatial intensity distribution of the laser beam that has been diffracted and scattered by the particles is detected by photodetector elements. From the results of measurement, a mathematical operation is carried out on the basis of the Fraunhofer diffraction theory or the Mie scattering theory so that the particle size distribution of the particles is calculated. This mathematical operation method on the basis of the Fraunhofer diffraction theory or the Mie scattering theory was obtained assuming that the laser beam is scattered only once by a particle. Therefore, the particle size distribution of particles can be calculated with high precision when the concentration of the particles in the medium is within an appropriate concentration range.

In the case where the concentration of particles in a medium is too high, however, the laser beam for irradiation is scattered by a certain particle so as to be a scattered beam, which is further scattered by another particle. Thus, multiple scatterings take place, which causes a large error between the calculated particle size distribution of the particles and the actual particle size distribution of the particles.

Accordingly, it is necessary to prepare a sample that is thin in the direction of the optical axis of the laser beam in order to reduce the occurrence of multiple scatterings of a beam in the case where the particle size distribution of particles is measured in a sample that contains a high concentration of particles, such as a paste or a slurry.

Here, an example of a laser diffraction-type particle size distribution measuring apparatus is described. FIG. 5 is a schematic diagram showing the structure of a conventional particle size distribution measuring apparatus. FIG. 4 is a schematic diagram showing the structure of an example of a sample cell. In FIG. 5, direction X is a direction that is parallel to the ground, direction Y is the direction that is parallel to the ground and perpendicular to direction X, and direction Z is an upward direction that is perpendicular to direction X and direction Y.

A particle size distribution measuring apparatus 109 is provided with a sample cell 5 in which a sample S is contained, a table (sample cell placing portion) 130 having a laser beam passing hole 130a, an optical system for irradiation 110 having a laser beam source 1, a collimator 2 and a transparent cover 3, an optical system for measurement 120 having a condenser lens 6 and a ring detector (forward diffraction and scattering optical sensor) 7, and a control unit 140 for controlling the entirety of the particle size distribution measuring apparatus 109 (see Patent Document 1).

In the lower portion of the particle size distribution measuring apparatus 109, the laser beam source 1, the collimator 2 and the transparent cover 3 are provided in this order from the bottom as part of the optical system for irradiation 110.

In the middle portion in the upward and downward directions of the particle size distribution measuring apparatus 109, the table 130 is provided and the sample cell 5 is placed on top of the table 130.

In this structure of the optical system for irradiation 110, the laser beam generated by the laser beam source 1 passes through the collimator 2 so as to be a parallel beam with which the sample cell 5 is irradiated when directed in the upward direction (direction Z). Here, the parallel beam has a cross-section in a circular shape that is perpendicular to the optical axis and has an area of approximately 1 $cm^2$. Thus, the laser beam is diffracted and scattered by the particles within the sample cell 5, thereby causing a spatial intensity distribution pattern of the diffracted and scattered beam.

In the upper portion of the particle size distribution measuring apparatus 109, the condenser lens 6 and the ring detector 7 are provided in this order from the bottom as part of the optical system for measurement 120. The ring detector 7 has a number (64, for example) of photodetector elements having a light receiving surface in ring form or semi-ring form having a radius that is different from each other arranged in a concentric form with the optical axis of the condenser lens 6 at the center, where each photodetector element allows a beam having a diffraction or scattering angle in accordance with its respective location to enter. Accordingly, the output signal of each photodetector element represents the intensity of the beam for each diffraction or scattering angle.

In this structure of the optical system for measurement 120, diffracted and scattered beams within 60° relative to the upward direction are condensed onto the light receiving surface of the ring detector 7 via the condenser lens 6 so as to focus into a diffraction and scattering image in ring form.

The sample cell 5 is provided with a transparent glass plate (first substrate) 11 in plate form (thickness: t, width: Y, length: X) and a transparent glass plate (second substrate) 13 in plate form (thickness: t, width: Y, length: X). A recess (recess for measurement) 12 in which a sample S is contained is created in the center portion on the upper surface of the glass plate 11. The recess 12 is in circular form having a cross-sectional area of approximately 1 $cm^2$ as viewed from the top, and the depth of the recess 12 is set at a certain distance $\Delta t$ (0.1 mm or greater and 0.5 mm or smaller, for example).

When the glass plate 13 is provided so that the lower surface of the glass plate 13 makes contact with the upper surface of the glass plate 11, the distance between the lower surface of the glass plate 13 and the bottom of the recess 12 equals the set distance $\Delta t$. Accordingly, this sample cell 5 can make the thickness of the sample S a predetermined thickness $\Delta t$, which is thin relative to the optical axis of the laser beam when the sample S is contained in the recess 12, and as a result, the beam can be prevented from scattering a multiple number of times.

PRIOR ART DOCUMENT

Patent Document

Patent Document 1: Japanese Unexamined Patent Publication H9 (1997)-72841

SUMMARY OF THE INVENTION

Problem to be Solved by the Invention

In the above-described particle size distribution measuring apparatus 109, the particle size distribution of particles in a small amount of sample S containing a high concentration of particles can be measured, and therefore, it is possible to use the particle size distribution measuring apparatus 109 in order to measure the scattering and aggregation properties of a protein because in many cases, proteins of biopharmaceuticals provide a small amount of sample S with a high concentration of particles. However, the scattering and aggregation properties of a protein differ depending on the temperature, and thus, an evaluation at various set temperatures (4° C. and the human body temperature, for example) is necessary. In the particle size distribution measuring apparatus 109, however, such problems arise that the sample S of a protein or the like cannot be maintained at a set temperature, and thus, the scattering and aggregation properties of the protein cannot be evaluated precisely because the cross-sectional area of the light path (recess 12) through which the laser beam or the diffracted and scattered beam pass is large, which makes the radiation of heat from the recess 12 great even when a temperature adjusting member (a metal plate having a Peltier element) is attached to the table 130.

In addition, in the above-described particle size distribution measuring apparatus 109, a small amount of sample S containing a high concentration of particles is measured, and therefore, it is impossible to attach a stirring mechanism within the recess 12 in the sample cell 5. Thus, other problems arise such that the temperature of the entire sample S is not uniform, and the temperature is different depending on the location of the sample S due to the viscosity of the sample S of a protein or the like, which creates almost no convection.

Therefore, an object of the present invention is to provide a particle size distribution measuring apparatus with which the particle size distribution of particles to be measured that are included in a sample can be calculated at a desired temperature.

Means for Solving Problem

In order to achieve the above-described object, the present invention provides a particle size distribution measuring apparatus, having: a light source for emitting light for measurement; a detector for detecting the light intensity distribution; a sample cell placing portion for placing a sample cell in which a sample including particles to be measured is contained along a light path between the light source and the detector; a light intensity distribution obtaining unit for obtaining the light intensity distribution that occurs when the sample is irradiated with the light for measurement from the above-described light source through detection by the detector; and a particle size distribution calculating unit for calculating the particle size distribution of the particles to be measured included in the above-described sample by using the light intensity distribution obtained by the above-described light intensity distribution obtaining unit, wherein the particle size distribution measuring apparatus further has a temperature adjusting member for adjusting the temperature of the above-described sample cell, the above-described temperature adjusting member is movable between a first location along the light path around the above-described sample cell and a second location that is outside the light path, and the above-described temperature adjusting member is moved to the second location when the sample is irradiated with the light for measurement from the above-described light source.

Effects of the Invention

In the particle size distribution measuring apparatus according to the present invention, the temperature adjusting member for the setting at a desired temperature is provided in the first location, and therefore, the sample can be maintained at the desired temperature when the sample is not irradiated with measuring light from the light source. When the sample is irradiated with measuring light from the light source, the temperature adjusting member is moved to the second location that is outside the light path by a person manually or automatically by the control unit. As a result, the particle size distribution of the particles to be measured that is included in the sample at a desired temperature can be calculated. Though the temperature adjusting member is moved to the second location when the sample is irradiated with measuring light from the light source, no problems arise because the time for measurement is short (several seconds, for example).

Other Means for Solving Problem and Working Effects

In the particle size distribution measuring apparatus according to the present invention, the above-described light intensity distribution obtaining unit may carry out the operation where the above-described temperature adjusting member is moved to the second location.

In the particle size distribution measuring apparatus according to the present invention, the light intensity distribution obtaining unit moves the temperature adjusting member to the second location when the sample is irradiated with measuring light.

In addition, in the particle size distribution measuring apparatus according to the present invention, the above-described sample cell may have a transparent first substrate in plate form and a transparent second substrate in plate form, a recess for measurement in which the above-described sample is contained may be created on an upper surface of the above-described first substrate, and the above-described second substrate may be provided so that a lower surface of the second substrate makes contact with an upper surface of the above-described first substrate so as to make the distance between the lower surface of the above-described second substrate and the bottom of the recess for measurement a set distance.

Here, the "set distance" is a distance that has been determined in advance by the designer of the sample cell or the like by taking the sample to be measured into consideration and is 0.1 mm or greater or 0.5 mm or smaller, for example. It is preferable for the set distance to be approximately the same as the maximum particle diameter of the particles included in the sample or to be approximately a few times (two to three times) greater than the maximum particle diameter.

Furthermore, in the particle size distribution measuring apparatus according to the present invention, the above-described temperature adjusting member may have a substrate in plate form of which the temperature can be adjusted, and the above-described substrate in plate form may be movable between a first location where the substrate in plate form is placed so as to make contact with the above-described first substrate or the above-described second substrate and a second location where the substrate in plate form is placed so as not to make contact with the above-described first substrate or the above-described second substrate.

PREFERRED EMBODIMENTS

In the following, preferred embodiments of the present invention are described in reference to the drawings. The present invention is not limited to the below-described embodiments, but includes various modifications as long as the gist of the present invention is not deviated from.

Figure 1:
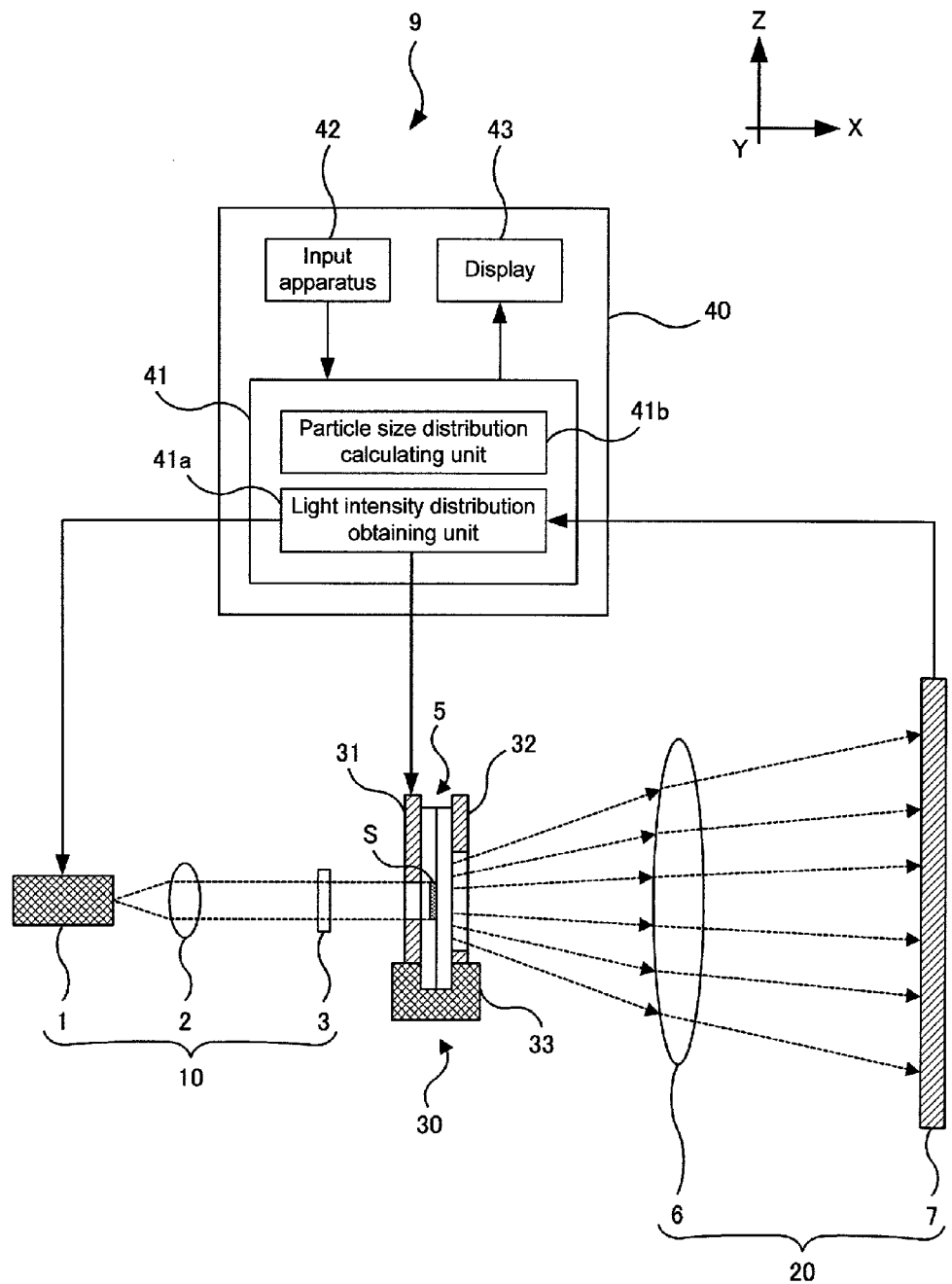
FIG. 1 is a schematic diagram showing the structure of an example of the particle size distribution measuring apparatus according to the present invention.
Figure 2:
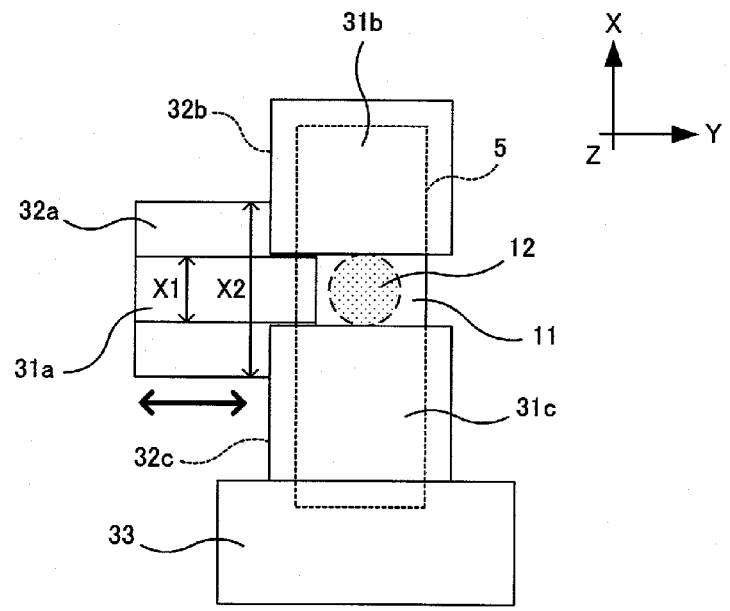
FIG. 2 is a front diagram showing the sample cell placing portion in FIG. 1.
Figure 3:
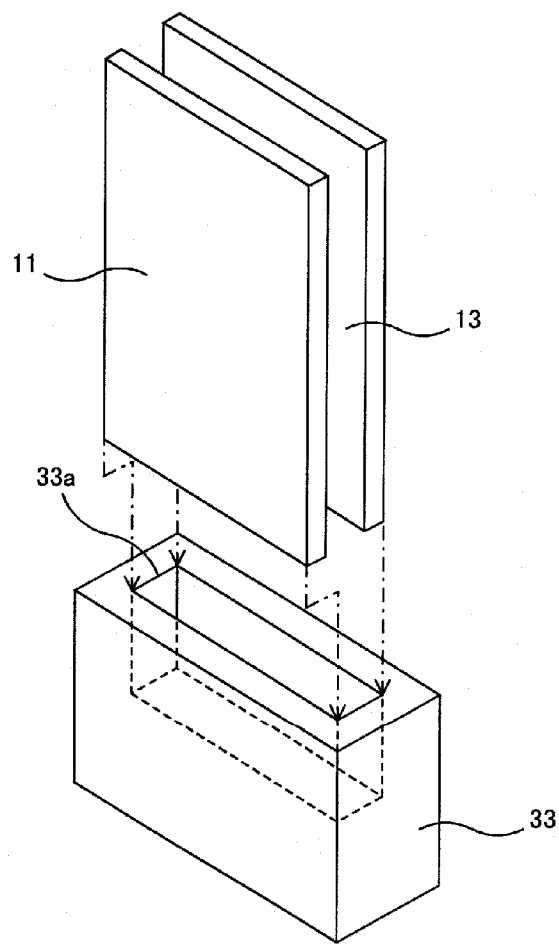
FIG. 3 is a perspective diagram showing the sample cell placing portion in FIG. 1.
Figure 4:
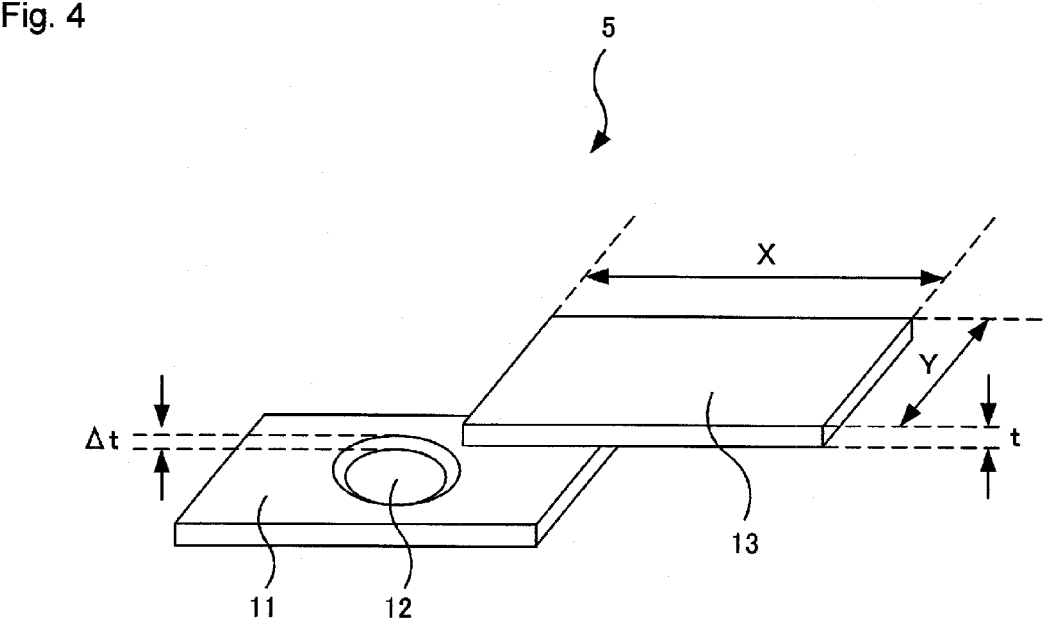
FIG. 4 is a schematic diagram showing the structure of an example of the sample cell.
Figure 5:
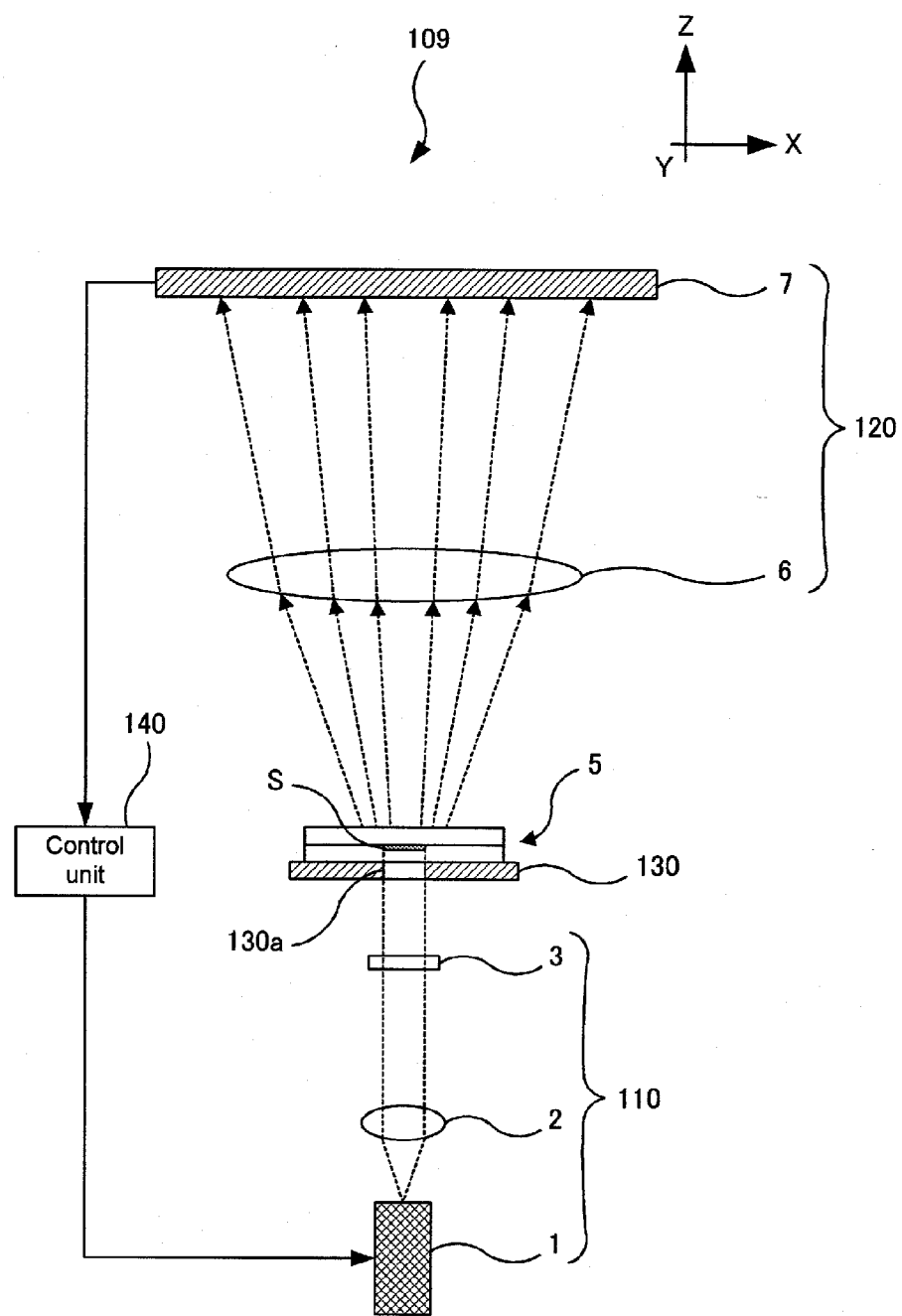
FIG. 5 is a schematic diagram showing the structure of a conventional particle size distribution measuring apparatus.

FIG. 1 is a schematic diagram showing the structure of an example of the particle size distribution measuring apparatus according to the present invention. FIG. 2 is a front diagram showing the sample cell placing portion in FIG. 1, and FIG. 3 is a perspective diagram showing part of the sample cell placing portion in FIG. 1. In FIG. 1, the direction Z is the direction to the right, which is one direction parallel to the ground, the direction Y is the direction parallel to the ground and perpendicular to the direction Z, and the direction X is the upward direction perpendicular to the direction Z and the direction Y. In addition, the same symbols are attached to the same components as in the above-described particle size distribution measuring apparatus 109.

The particle size distribution measuring apparatus 9 is provided with a sample cell 5 in which a sample S is contained, a sample cell placing portion 30 on which the sample cell 5 is placed, an optical system for irradiation 10 having a laser beam source 1, a collimator 2 and a transparent cover 3, an optical system for measurement 20 having a condenser lens 6 and a ring detector (forward diffraction and scattering photosensor) 7, and a control unit 40 for controlling the entirety of the particle size distribution measuring apparatus 9.

The laser light source 1, the collimator 2 and the transparent cover 3 are provided in this order from the left as part of the optical system for irradiation 10 in the left portion of the particle size distribution measuring apparatus 9. In this structure of the optical system for irradiation 10, the laser beam generated by the laser light source 1 passes through the collimator 2 so as to be a parallel beam with which the sample cell 5 is irradiated when directed to the direction to the right (direction Z). Here, the parallel beam has a cross-section in circular form that is perpendicular to the optical axis and has an area of approximately 1 cm$^2$.

The condenser lens 6 and the ring detector 7 are provided in this order from the left as part of the optical system for measurement 20 in the right portion of the particle size distribution measuring apparatus 9. The ring detector 7 has a number (64, for example) of photodetector elements having a light receiving surface in ring form or semi-ring form having a radius that is different from each other arranged in a concentric form with the optical axis at the center, where each photodetector element allows a beam having a diffraction or scattering angle in accordance with its respective location to enter. Accordingly, the output signal of each photodetector element represents the intensity of the beam for each diffraction or scattering angle. In this structure of the optical system for measurement 20, diffracted and scattered beams within 60° from the optical axis are condensed onto the light receiving surface of the ring detector 7 via the condenser lens 6 so as to focus into a diffraction and scattering image in ring form.

The sample cell placing portion 30 is provided in the center portion of the particle size distribution measuring apparatus 9 in the left to right direction. The sample cell placing portion 30 is provided with an attachment member 33 on the upper surface of which a recess 33a is created, and a temperature adjusting member 31, 32 for adjusting the temperature of the sample cell 5.

The lower end portion of the sample cell 5 is inserted into the recess 33a of the attachment member 33. As a result, a recess 12 of the sample cell 5 is provided along the light path between the laser beam source 1 and the ring detector 7.

The temperature adjusting member 31, 32 is provided with a front plate 31 in plate form (width: Y+β, length: X+α) and a rear plate 32 in plate form (width: Y+β, length: X+α). The front plate 31 is provided so as to stand on the upper surface of the attachment member 33 and make contact on the front (left) side of the glass plate (second substrate) 13 of the sample cell 5 that has been inserted into the recess 33a of the attachment member 33, and the rear plate 32 is provided so as to stand on the upper surface of the attachment member 33 and make contact on the rear (right) side of the glass plate (first substrate) 11 of the sample cell 5 that has been inserted into the recess 33a of the attachment member 33.

The front plate 31 has an upper fixed jacket portion 31b in plate form, a middle shutter portion (substrate in plate form) 31a in plate form (width: Y+β, length: X$_1$) that is movable between a first location and a second location, and a lower fixed jacket portion 31c in plate form. The first location is located along the light path between the laser beam source 1 and the ring detector 7, the second location is located outside the light path between the laser light source 1 and the ring detector 7, and the middle shutter portion 31a can slide in the direction Y to the first location or to the second location in response to the control signal from the control unit 40.

In addition, the middle shutter portion 31a, the upper fixed jacket portion 31b, and the lower fixed jacket portion 31c are made of a metal plate or the like having a Peltier element, a certain type of heater, and a constant temperature tank with pipes for circulation being connected so that the temperature can be adjusted to a desired temperature by the control signal from the control unit 40.

The rear plate 32 has an upper fixed jacket portion 32b in plate form, a middle shutter portion (substrate in plate form) 32a in plate form (width: Y+β, length: X$_2$) that is movable between a first location and a second location, and a lower fixed jacket portion 32c in plate form. The first location is located along the light path between the laser beam source 1 and the ring detector 7, the second location is located outside the light path between the laser light source 1 and the ring detector 7, and the middle shutter portion 32a can slide in the direction Y to the first location or to the second location in response to the control signal from the control unit 40. Here, diffracted and/or scattered light is emitted from the recess 12 of the sample cell 5, and therefore, the length X$_2$ of the middle shutter portion 32a is greater than the length X$_1$ of the middle shutter portion 31a.

In addition, the middle shutter portion 32a, the upper fixed jacket portion 32b, and the lower fixed jacket portion 32c are made of a metal plate or the like having a Peltier element, a certain type of heater, and a constant temperature tank with pipes for circulation being connected so that the temperature can be adjusted to a desired temperature by the control signal from the control unit 40.

The control unit 40 is provided with a CPU 41, and furthermore, a display 43 having a monitor screen and the like and an input apparatus 42 having a keyboard, a mouse, and the like are linked to the control unit 40. The functions processed by the CPU 41 can be described as blocks wherein a light intensity distribution obtaining unit 41a for obtaining the light intensity distribution through detection by the ring detector 7 and a particle size distribution calculating unit 41b for calculating the particle size distribution of particles to be measured are provided.

The light intensity distribution obtaining unit 41a controls the system such that the light intensity distribution resulting from the irradiation of the sample S with a laser beam from the laser beam source 1 is obtained through detection by the ring detector 7 immediately after the middle shutter portions 31a and 32a of the temperature adjusting member 31, 32 have been moved to the second location.

For example, the middle shutter portion 31a of the temperature adjusting member 31 is first located in the first location, and at the same time, the middle shutter portion 32a of the temperature adjusting member 32 is located in the first location. Next, the set temperature is inputted by using the input apparatus 42 so that the temperature of the middle shutter portion 31a, the upper fixed jacket portion 31b, and the lower fixed jacket portion 31c is set to the set temperature, and at the same time, the temperature of the middle shutter portion 32a, the upper fixed jacket portion 32b, and the lower fixed jacket portion 32c is set to the set temperature. Next, the lower end portion of the sample cell 5 is inserted. Thus, the sample S is irradiated with a laser beam from the laser beam source 1 immediately after the middle shutter portion 31a of the temperature adjusting member 31 has been slid to the second location, and at the same time, the middle shutter portion 32a of the temperature adjusting member 32 is slid to the second location when the temperature of the sample S becomes a desired temperature. As a result, the light intensity distribution is obtained through detection by the ring detector 7.

The particle size distribution calculating unit 41b controls the system such that the particle size distribution of particles to be measured is calculated using the light intensity distribution obtained by the light intensity distribution obtaining unit 41a.

As described above, the particle size distribution measuring apparatus 9 makes it possible to calculate the particle size distribution of particles to be measured that is included in the sample S at a desired temperature.

Other Embodiments (1) Though the above-described particle size distribution measuring apparatus 9 has the structure where the temperature adjusting member 31, 32 is provided on the front and rear sides of the sample cell 5, the structure may be such that the temperature adjusting member is provided only on one side of the sample cell 5.

(2) Though the above-described particle size distribution measuring apparatus 9 has the structure where the front plate 31 and the rear plate 32 have an upper fixed jacket portion, a middle shutter portion, and a lower fixed jacket portion, the structure may be such that the upper fixed jacket portion, the middle shutter portion, and the lower fixed jacket portion are integrated, and all the portions move together.

(3) Though the above-described particle size distribution measuring apparatus 9 has the structure where the light intensity distribution obtaining unit 41a moves the middle shutter portions 31a and 32a of the temperature adjusting member 31, 32 to the second location, the structure may be such that the middle shutter portions 31a, 32a of the temperature adjusting member 31, 32 may be moved to the second location by a person manually.

INDUSTRIAL APPLICABILITY

The present invention can be applied to a laser diffraction-type particle size distribution measuring apparatus for measuring the particle size distribution of particles in a sample.

EXPLANATION OF SYMBOLS

1: laser light source
5: sample cell
7: ring detector
9: laser diffraction-type particle size distribution measuring apparatus
30: sample cell placing portion
31, 32: temperature adjusting member
41a: light intensity distribution obtaining unit
41b: particle size distribution calculating unit

What is claimed is:

1. A particle size distribution measuring apparatus, comprising:
    a light source for emitting light for measurement;
    a detector for detecting the light intensity distribution;
    a sample cell placing portion for placing a sample cell in which a sample including particles to be measured is contained along a light path between the light source and the detector;
    a light intensity distribution obtaining unit for obtaining the light intensity distribution that occurs when the sample is irradiated with the light for measurement from said light source through detection by the detector; and
    a particle size distribution calculating unit for calculating the particle size distribution of the particles to be measured included in said sample by using the light intensity distribution obtained by said light intensity distribution obtaining unit, characterized by further comprising:
    a temperature adjusting member for adjusting the temperature of said sample cell, wherein
    said temperature adjusting member is movable between a first location along the light path around said sample cell and a second location that is outside the light path, and
    said temperature adjusting member is moved to the second location when the sample is irradiated with the light for measurement from said light source.

2. The particle size distribution measuring apparatus according to claim 1, characterized in that said light intensity distribution obtaining unit carries out the operation where said temperature adjusting member is moved to the second location.

3. The particle size distribution measuring apparatus according to claim 1, characterized in that
    said sample cell comprises a transparent first substrate in plate form and a transparent second substrate in plate form,
    a recess for measurement in which said sample is contained is created on an upper surface of said first substrate, and
    said second substrate is provided so that a lower surface of the second substrate makes contact with an upper surface of said first substrate so as to make the distance between the lower surface of said second substrate and the bottom of the recess for measurement a set distance.

4. The particle size distribution measuring apparatus according to claim 3, characterized in that
    said temperature adjusting member comprises a substrate in plate form of which the temperature can be adjusted, and
    said substrate in plate form is movable between a first location where the substrate in plate form is placed so as to make contact with said first substrate or said second substrate and a second location where the substrate in plate form is placed so as not to make contact with said first substrate or said second substrate.

* * * * *